United States Patent [19]

Ciorbaru et al.

[11] 4,042,678

[45] Aug. 16, 1977

[54] WATER-SOLUBLE AGENTS HAVING MITOGENIC PROPERTIES OBTAINED FROM NOCARDIA CELLS, AND PROCESSES FOR THE PREPARATION THEREOF

[75] Inventors: Rita, born Sfartz Ciorbaru, Fontenay aux Roses; Arlette, born Chosson Adam, Palaiseau; Jean-Francois Petit, Paris; Edgar Lederer, Sceaux; Chantal, born Rousselot Damais, Le Vesinet; Louis Chedid; Constantin Bona, both of Paris, all of France

[73] Assignee: Agence Nationale de Valorisation de la Recherche (ANVAR), Neuilly-sur-Seine, France

[21] Appl. No.: 571,384

[22] Filed: Apr. 24, 1975

[30] Foreign Application Priority Data

Apr. 25, 1974   France ................................ 74.14500

[51] Int. Cl.$^2$ ............................................. A61K 39/02
[52] U.S. Cl. ......................................... 424/12; 195/2; 424/92

[58] Field of Search ................ 424/92, 195, 12; 195/2

[56] References Cited

PUBLICATIONS

Adam et al., –Chem. Abst. vol. 79, (1973), p. 30388f.
Adam et al., Chem. Abst. vol. 82, (1975), p. 137479a (abst of a 1974 article).

*Primary Examiner*—Sam Rosen
*Attorney, Agent, or Firm*—Weiser, Stapler & Spivak

[57] ABSTRACT

The invention pertains to a mitrogenic agent and to a process for obtaining same.

It comprises the steps of cultivating Nocardiae cells, collecting them, subjecting them to a treatment for rupturing the integrity of their walls, such as by lysis, discarding the solid residue and collecting the aqueous fraction, causing the peptidoglycane fragments contained in this aqueous fraction to be separated therefrom and recovering the remaining fraction containing the mitogenic agent.

22 Claims, 4 Drawing Figures

WATER-SOLUBLE AGENTS HAVING MITOGENIC PROPERTIES OBTAINED FROM NOCARDIA CELLS, AND PROCESSES FOR THE PREPARATION THEREOF

The invention relates to soluble agents having mitogenic properties. These properties make the agents very valuable biological tools in research and diagnosis. When administered to man or animals, these agents induce a non-specific stimulation of B lymphocytes, producing an increase in antibodies directed against large classes of antigens. Furthermore, they promote the development of stem-cells and accordingly their use can be considered in the curative treatment of illnesses resulting from deficiencies of immunocompetent and haematopoietic cells.

Agents capable of stimulating lymphocyte cultures in vitro and also stem-cells, have already been described. These agents are basically lipoplysaccharides or bacterial endotoxins which stimulate the stem-cells and exert a mitogenic activity in vitro with regard to B lymphocytes from mouse spleen. However, they are inactive with regard to B lymphocytes of many other species of animals including, in particular, rabbits, monkeys, and man. In any case, their extreme toxicity would preclude the therapeutic application of these lipopolysaccharides (designated hereinafter by the abbreviations LPS) in man or animals.

The object of the invention is to provide agents which are active in vivo and are also non-toxic, and which can be used for therapeutic applications on the one hand, and non-therapeutic applications on the other hand.

The invention is based on the discovery that non-toxic preparations having a mitogenic adjuvant and stimulating action on haematopoietic cells can be obtained from Nocardia cells. Furthermore, this non-specific mitogenic activity has been demonstrated, not only in mice, but also, in other animal species, including man. More particularly it has been found that preparations having a mitogenic activity could be obtained by applying to the Nocardia cells known processes for extracting hydrosoluble agents having a non-specific immunostimulant activity, such as those disclosed in the U.S. patent applications Ser. Nos. 307,614 and 371,512 filed respectively on Nov. 17, 1972 and June 19, 1973 now U.S. Pat. No. 3,976,544.

In a general manner, crude preparations having mitogenic activity can be obtained by resorting to a process which comprises cultivating a strain of Nocardiae, recovering the cells from said culture of Nocardiae, subjecting said cells within an aqueous solution to a treatment likely to cause rupturing of the integrity of the cell walls, such as by lysis, separating the solid residue and recovering the aqueous solution obtained which constitutes the above said crude mitogenic preparation.

More purified mitogenic preparations are obtainable by subjecting said crude preparation to filtration on a molecular sieve and by recovering those of the fractions which contain the mitogenic agent. Generally, these fractions are also those which contain peptidoglycane fragments too.

For instance it has been found that immuno-stimulant agents extracted from Nocardiae by resorting to extraction processes such as those described in the first patent referred to hereabove, or preferably, such as those described in the above second application, contain such a mitogenic agent.

It will be recalled that the process described in the main patent application mentioned above consists essentially, in particular when applied to Nocardia cells, of cultivating these cells, collecting the cells of the cultivated strain, rupturing the cells, recovering the ruptured cell walls, for example by differential centrifugation. separating and eliminating the waxes, free lipids, proteins and nucleic acids, digesting the delipidated material from the cell walls with a murolytic enzyme such as lysozyme, in an aqueous medium, and finally removing the solid residue and collecting the aqueous fraction which contains the non-specific immunological adjuvant agents.

According to the improved process described in the said certificate of addition application, which is a preferred process, the collected cultivated cells are directly treated with delipidation solvents, without any previous treatment, in order to rupture them, and the delipidated cells are then directly subjected to the action of the murolytic enzyme. Like the process described in the main patent application, the process of the certificate of addition application enables an aqueous fraction containing a hydrosoluble immunostimulant agent which can be lyophilised to be obtained, particularly from Nocardiae cells. These aqueous fractions also contain other mitogenic agent.

In the first variation of the process referred to hereabove the following procedures can be resorted to for separating and eliminating the waxes, the free lipids, the proteins and the nucleic acids. Preferably, the cumbersome proteins are eliminated by treating the material of the disrupted cell walls with proteolitic enzymes such as trypsin and chymotrypsin, the nucleic acids are eliminated by treatment of the said material with Desoxyribonuclease of DNAse, the free lipids and waxes are eliminated by treatment of this material with neutral solvents such as, for instance, aceton, alcohol, chlorform or mixtures of such solvents, advantageously under reflux in an extractor of the Soxhlet or Kumagawa type.

Of course the delipidation of the whole cells in the second variation of the process referred to hereabove can be carried out in the same manner with analogous solvents.

The cell walls or, preferably, the whole delipidated cells (depending upon the extraction process used) are washed thereafter and suspended in water or in an aqueus solution, pH of this medium being then adjusted; as well known, to the values which will enable the murolytic enzyme used thereafter to exert its digestion action under optimized conditions. When the enzyme used is lysozyme, the pH will advantageously be adjusted to a value of about 6.2 – 6.3. In the latter instance, use is advantageously made of an ammonium acetate buffer 0.1 M at pH 6.2, which buffer not only enables lysozyme to exert its action under optimized conditions, but also can thereafter be totally eliminated, such as by lyophilisation of the medium.

It will be understood that generally and as is well known the pH authorizing the optimized working conditions of the enzyme may vary depending upon the nature of the selected murolytic enzyme, possibly, in some cases, upon the nature of the substrate. If need be this pH value, as well as the preferred digestion temperature, will be determined experimentally.

The hydrosoluble immuno-stimulant agent obtained is advantageously purified, particularly by taking up the lyophilised agent in an aqueous solution, enabling it to be filtered through a molecular sieve, for example in dilute acetic acid. Molecular sieves of the type sold under the brand names SEPHADEX, particularly SEPHADEX G 75 and G50, are advantageously used. The fractions which exhibit a mitogenic activity are then recovered. Generally such fractions are also those which contain peptidoglycane fragments either free or chemically bound.

It is known that other authors have described other processes enabling similar hydrosoluble agents to be obtained from mycobacteria. The publications of MIGLIORE D. and JOLLES T. (1972), FEBS Letters, 25. 301–304 and of HIU I.J. (1972), Nature New Biology, 238, 241–242, may be mentioned for the sake of recollection. The processes described in these publications may of course be applied to Nocardia cells.

The adjuvant activity of the preparations in question has been attributed, inter alia, to soluble fragments of peptidoglycanes forming part of the constitution of the cell walls of the bacteria initially used, contained in these preparations.

It has also been found according to the invention that the hydrosoluble Nocardiae preparations also contain a mitogenic agent different from the peptidoglycane fragments mentioned above. In addition it has been found that the Nocardiae preparations contain other adjuvants which do not appear to consist of peptidoglycane fragments.

These agents form the subject of the present invention, as do processes for their extraction from hydrosoluble preparations of the type recalled above.

The invention also relates to new therapeutic applications and applications in non-therapeutic fields, which will be considered later, of the hydrosoluble preparations of the type in question when obtained from a Nocardiae culture.

The products according to the invention are those obtained from these hydrosoluble preparations or from fractions obtained by purifying these hydrosoluble preparations, particularly by filtration through a molecular sieve, preferably of the SEPHADEX type, after having substantially separated the peptidoglycane fragments or the adjuvant agents containing the peptidoglycane fragments either free or chemically bound, initially contained in these preparations or fractions.

One of the processes according to the invention, which is applied to hydrosoluble preparations of the type in question and extracted from Nocardiae or from purified fractions of the latter, particularly by filtration through a molecular sieve, essentially consists of separating the peptidogylcane fragments and receovering the remaining products which contain the mitogenic agent according to the invention.

According to a variation of the process, fractions containing the mitogenic agent are extracted by washing delipidated Nocardiae with water, the wash liquids containing the mitogenic agent.

In accordance with the preferred embodiment of the process according to the invention, the hydrosoluble preparations of the type in question or purified fractions thereof are lyophilised, the lyophilisates are suspended in concentrated acetic acid, that is either, and preferably, pure acetic acid, or an aqueous acetic acid solution containing at least 70% and at least 90% by weight of acetic acid and the dissolved fraction is separated from the undissolved fraction, such as by centrifugation, the dissolved fraction then being discarded and the undissolved fraction being recovered. The fraction insoluble in concentrated acetic acid, which may however be redissolved without difficulty in water, contains the mitogenic agent according to the invention. It is active in vitro and in vivo with respect to many animal species, including man.

In addition, the hydrosoluble preparations mentioned above are preferably subjected to solvent extractions in order to complete their delipidation, before being lyophilised and taken up in water.

The remarkable fact that the mitogenic hydrosoluble product is active in the absence of any addition of an oily carrier should also be emphasised. It may therefore be used in the form of aqueous solutions. Furthermore, it is not toxic.

Other special features of the invention will appear in the course of the description which follows of several mitogenic agents obtained from cultures of several Nocardiae, particularly *Nocardia opaca*, *Nocardia corallina* and *Nocardia rubra* (*Corynebacterium rubrum* according to some authors).

The culture conditions for the strains taken as examples and the conditions for obtaining active fractions will be described hereinafter.

The cells of three strains of Nocardiae are cultivated in a fermenter of 20 liters volume (Biolafitte, Maisons-Lafitte).

*Nocardia opaca*, Pasteur strain (ATCC 21953) is cultivated for 2 days at 30° C in a medium comprising 0.2% yeast extract (Difco), 0.4% meat extract (Difco), 2% bactopeptone (Difco) and 0.5% NaCl, the pH having been adjusted to 7.2.

*Nocardia corallina*, 999 ATCC strain, is cultivated for 24 hours at 34° C in a medium comprising 0.4% meat extract (Difco), 2% bactopeptone (Difco) and 0.5% NaCl, the pH having been adjusted to 7.2.

*Nocardia rubra*, 14898 ATCC strain, is cultivated for 5 days in a medium comprising 2.5% "Heart Infusion Broth" Difco), 10 ml/liter of glycerol and 0.25 g/liter of $Na_2HPO_4.12H_2O$, the pH having been adjusted to 7.4–7.6.

The cells are delipidated in a Soxhlet extractor by, in succession, acetone, ethanol, ether, chloroform, methanol and a chloroform-methanol mixture (87:13) (v/v), and are then resuspended in acetone, decanted, and dried.

The cells are next extracted with one hundred times their weight of water by being brought into suspension using a Protter grinder having a teflon piston; the supernatant is recovered by centrifugation (1 hour, 27.500 g, at 4° C) and lyophilised. The lyophilised extract is both adjuvant and mitogenic. The cells are then extracted with one hundred times their weight of 0.1M ammonium acetate, the pH being 6.2. They are finally suspended in 100 times their weight of ammonium acetate (0.1M), pH 6.2, containing 0.01% of chicken eggwhite lysozyme (Industrie biologique francaise, 93-Gennevilliers), a few drops of toluene having been added to prevent contamination, and are reincubated under the same conditions. The two extracts are mixed and lyophilised, then taken up in water and re-lyophilised several times to remove ammonium acetate, the resulting product being called "crude lysozyme extracts".

The "crude lysozyme extracts" of the three strains are delipidated by successive extractions at normal temperature, once with ether and three times with chloroform-methanol (2:1, v/v). They are then taken up in ether and dried.

400 mg of delipidated extract are placed on a SEPHADEX G75 columns (h = 80 cm, diameter 2.5 cm), equilibrated with 0.1M acetic acid, and eluted with this same solution. The following are determined in the effluent from the column: neutral sugars (by the orcinol method), aminoacids (by measurement with ninhydrin after alkaline hydrolysis) and amine sugars (after acid hydrolysis by the Elson Morgan method), which enables the delipidated lysozyme filtrates to be fractionated into three fractions in the case of N.opaca, and into four fractions in the case of the other two strains, these fractions being called, K, L, M or K, L, M, N after their order of elution.

With the exception of the N fraction of *Nocardia rubra,* which is found to be only slightly mitogenic, all the other fractions are found to be adjuvant and mitogenic.

After previously having been lyophilised, the K fraction of N.opaca is subjected to an acid fractionation in order to separate the mitogenic and adjuvant activities; it is suspended in concentrated acetic acid and centrifuged (1 hour at 48.000 g) in a cooled centrifuge to give a deposit and a supernatant. The deposit is washed several times by being suspended and centrifuged in acetic acid. The mixed supernatants and deposit are finally lyophilised to give two fractions, both of which are adjuvant, but only the deposit is mitogenic. The deposite is redissolved in water.

The non-mitogenic fraction, soluble in concentrated acetic acid, is hereinafter called "fraction P", and the mitogenic fraction derived from the said deposit is called "fraction Q". Also, the K fraction of N.opaca is hereinafter called "NWSM" (abbreviation for "Nocardia Water-Soluble Mitogen"); reference will also sometimes be made to "supernatant" and to "deposit" in connection with fractions P and Q respectively, these expressions recalling the states in which they were isolated during the operation of the process according to the invention, particularly during the suspension of the K fraction of N.opaca (or NWSM) in concentrated acetic acid.

Table I below gives the analysis results for fractions P and Q.

TABLE I

| Fractions | Neutral sugars | Amine sugars | Aminoacids |
|---|---|---|---|
| | % | % | % |
| Deposit | 19-25 galactose, glucose | 10-12 glucosamine traces of muramic acid | 45-48 |
| Supernatant | 37-40 galactose, glucose, traces of ribose. | 32-35 glucosamine, muramic acid | 18-20 |

In all the fractions studied, with the exception of fractions N of N.rubra and the part Q of N.opaca, the presence of diamino-pimelic acid (DAP), which is a specific constituent of peptidoglycane, would indicate that their adjuvant activity is due to fragments of this macromolecule. The fraction N of N. rubra is also characterised by an adjuvant action which is evident from the results mentioned hereinafter with respect to the pharmacological tests of which it forms the subject. The absence of DAP shows that N.rubra produces an adjuvant whose chemical structure belongs to a different category of molecules.

In vitro and in vivo pharmacological properties of the fractions studied.

The results of the pharmacological tests carried out with the fractions studied are given hereinafter. With regard to the mitogenic activity of some of the fractions, reference will be made to the figures in the attached drawings, in which.

Figure 1:
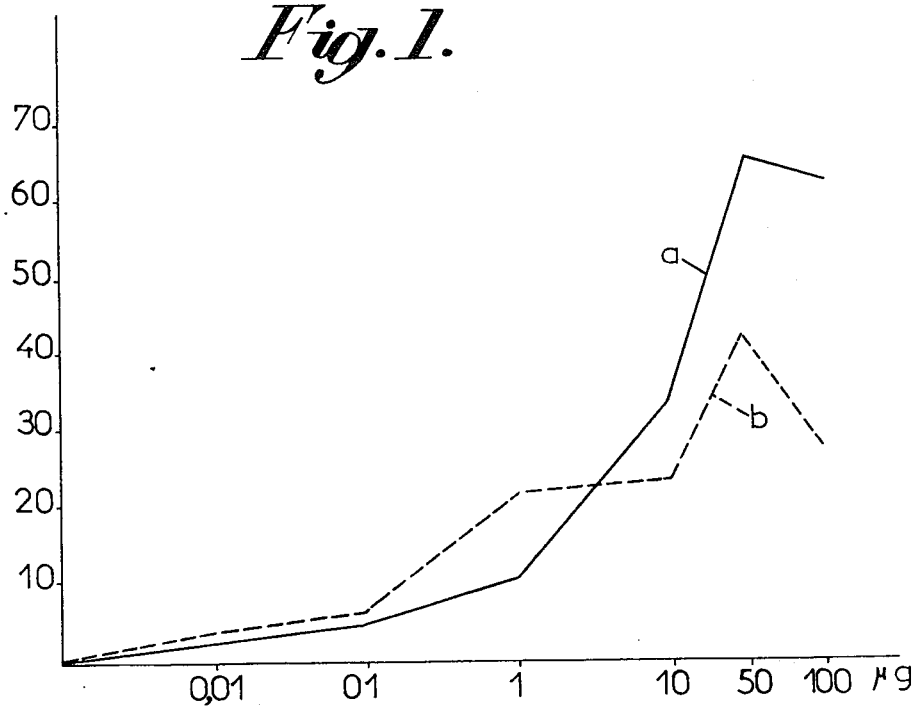
FIG. 1 shows curves giving the comparative stimulations of mouse spleen cells at different dosages of N.opaca mitogenic extract on the one hand, and S. enteridis LPS on the other hand.

I: Details regarding the adjuvant action of the various fractions studied

Female Hartley guinea pigms weighing 300-350 g were injected in the pad of each rear paw with a water-in-oil emulsion containing equal parts of a solution of ovalbumin (50mg/ml) of isotonic solution) and either a Freund complete adjuvant (FCA) or a Freund incomplete adjuvant (FIA) containing (with the exception of the control preparation) the fractions studied at the dosages mentioned in Table II hereinafter.

The adjuvant activity was estimated under the following conditions:

1. Determination in samples of serum taken 21 days after the injection, of the antibody titre expressed in $\mu$g/ml of serum of the antigen-antibody precipitate at the equivalence point;

2. Measurement of the delayed hypersensitivity to ovalbumin (dosages of 10 and 100 $\mu$g) in other animals, by cutaneous reaction 4 weeks after the injection, this is expressed by the diameter in mm of the erythema (E), hardening (I) and necrosis (N) 48 hours after the injection of ovalbumin.

TABLE II

| Fractions tested | Dosage ($\mu$g/anim) | Antibody titre in anim. A to E in $\mu$g/ml | | | | | aver- age | Delayed sensitivity to album. dosage of | |
|---|---|---|---|---|---|---|---|---|---|
| | | A | B | C | | E | | 10 $\mu$g | 100 $\mu$g |
| FIA | 0 | 900 | 560 | 700 | 600 | 480 | 660 | 8  I | 12 I |
| M. butyricum (FCA) | 50 | 2880 | 4800 | 3600 | 2800 | 3000 | 3416 | 13  I | 19/6 |
| N opaca K | " | 6700 | 4720 | 6200 | 3200 | | 5205 | 8  I | 21/4 |
| L | " | 5200 | 4100 | 4050 | 3620 | | 4270 | 9  I | 15/3 |
| M | " | 4100 | 2900 | 3100 | 2700 | | 3400 | 8  I | 20/5 |
| N opaca deposit Q | " | 1680 | 3920 | 3680 | 3660 | | 3235 | 8  I | 18/4 |
| super- P natant | " | 4000 | 4800 | 5120 | 6000 | | 4980 | 7  I | 18/6 |
| N. rubra K | " | 4800 | 5880 | 2700 | 3300 | 6600 | 4656 | 12  I | 21/4 |
| L | " | 5700 | 3900 | 5400 | 3300 | 4080 | 4476 | 8  I | 19/7 |
| M | " | 5700 | 5400 | 2820 | 5520 | 4500 | 4778 | 11  I | 21/5 |

TABLE II-continued

| Fractions tested | Dosage (µg/anim) | Antibody titre in anim. A to E in µg/ml | | | | | aver- age | Delayed sensitivity to album. dosage of | |
|---|---|---|---|---|---|---|---|---|---|
| | | A | B | C | | E | | 10 µg | 100 µg |
| N | " | 3000 | 2700 | 4000 | 3600 | 3060 | 3272 | 9    I | 17/6 |
| N. corallina | | | | | | | | | |
| K | " | 5400 | 5460 | 4800 | 2700 | 4500 | 4572 | 6    I | 18/7 |
| L | " | 4500 | 5340 | 4620 | 5400 | 4500 | 4716 | 7    I | 12/5 |
| M | " | 4740 | 4200 | 5160 | 5220 | 4560 | 4588 | 7    I | 12/5 |
| N | " | 3300 | 2100 | 4200 | 3060 | 3600 | 3252 | 9    I | 16/5 |

Table II shows that all the fractions, including the fractions N of N.rubra and the fraction Q (deposit) are adjuvant.

II. Details regarding mitogenic activity of hydrosoluble extracts of Nocardiae

Non-specific stimulation of the lymphocyte B cells derived from bone marrow: details of activity with regard to spleen lymphocytes from mice, rabbits, monkeys and man.

Lymphocytes culture

Lymphocytes are separated from the spleen of mice, rabbits, monkeys and man and cultivated in accordance with the techniques of Bona, C. Trebiciavsky, Anteunis, A., Heuclin, C. and Robineux R. Eur. J. Imm., 2. 434. 1972. In the case of the rabbit, monkey and man, I.5 × 10⁶ lymphocytes were cultivated in 1 ml of Eagle medium to which 10% of autologous serum (previously decomplemented) had been added in the first two cases, or in a pool of human AB serum. In the case of mice the same number of cells was cultivated in 1 ml of RPMI (Eutroph) to which 5% of foetal calf serum (Flow Labs) had been added. The cultures are made in an incubator in an air mixture containing 5% $CO_2$, for 2 days for mice cultures, 3 days for rabbit cultures and 5 days in the case of monkey and human cultures.

The lymphocyte cultures were stimulated by varying dosages fo the hydrosoluble adjuvant agent extracted from Nocardiae in accordance with the process described in the above-mentioned certificate of addition application N° 72 22120. In some experiments N. tuberculosis bovis or M. smegmatis tuberculins were used as controls (LPS), which are known mitogens of B lymphocytes of mouse spleen.

Incorporation of tritium-containing thymidine

1 µCi of $^3$H-thymidine (1Ci/mMole, Saclay, France) was added to the culture 24 hours before the cells were harvested. At the end of incubation, an amount of non-radioactive thymidine 100 times greater than the radioactive amount is added. After centrifugation at 450 G for 10 minutes, the supernatant is removed and the deposit is precipitated with trichloracetic acid and resuspended by conventional methods before being measured in a scintillation counter.

A. Mitogenic activity of a hydrosoluble extract of Nocardia opaca on spleen lymphocytes from mice and rabbits As can be seen from Table III, the Nocardia extract and also the LPS increase the incorporation of tritiated thymidine by spleen lymphocytes from mice, whereas the tuberculin does not show any activity.

| Stimulant added to 1.5 × 10⁶ cells | Dos- ages | No of mice tested | Stimulation index (1) | Significance of the stimulation ind. (2) | | |
|---|---|---|---|---|---|---|
| | | | | p 0.01 | p 0.05 | N.S. |
| Tuberculin M. tuberculis bovis). | 25 | 6 | 1.86 ± 0.6 | 0 | 1 | 5 |
| Nocardia opaca extract | 10 | 14 | 22.1 ± 10.4 | 11 | 2 | 1 |
| | 50 | 2 | 38.2 | 2 | 0 | 0 |
| LPS (S. minnesota) | 10 | 3 | 12.2 ± 3.1 | 3 | 0 | 0 |
| | 50 | 11 | 22.5 ± 3.9 | 9 | 1 | 1 |

(1) mean ± standard deviation
(2) the significance of the stimulated cells to that of the control cells was calculated by Student test for each animal.

Figure 2:
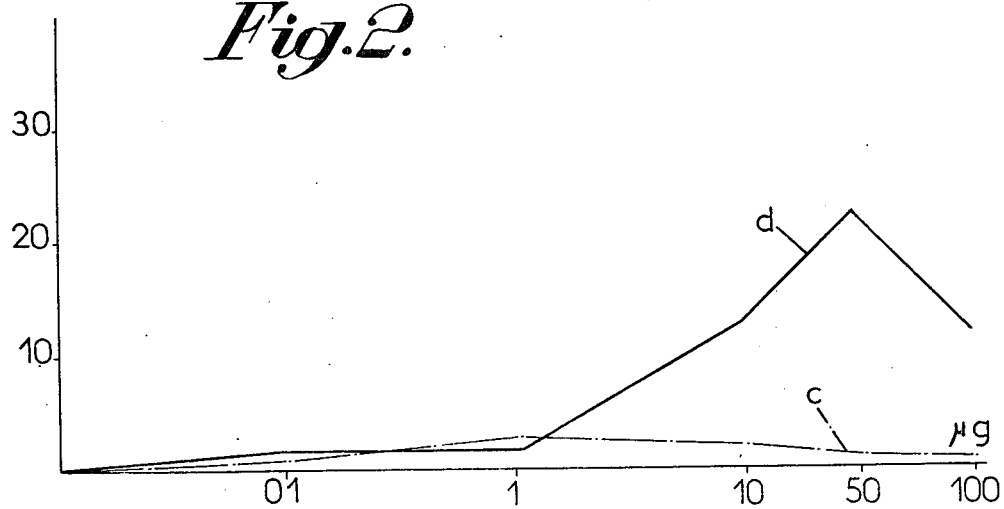
FIG. 2 shows the curves giving the comparative stimulations of rabbit spleen cells by the same mitogenic extracts.

A comparison of the dosage effects of the Nocardia extract and the endotoxin confirms that a larger stimulation is obtained with the Nocardia extract (FIG.1). The curves a and b of FIG. 1 are representative of the variations in the stimulation indices obtained with the N.opaca extract on the one hand, and with the LPS on the other hand, as a function of their respective dosages µg). In addition, in contrast to what was observed with LPS (curve c), the Nocardia mitogen (curve d) stimulates the incorporation of thymidine by rabbit lymphocytes (FIG. 2).

B. Nature of the lymphocytes sensitive to the mitogen

Other experiments have shown that the effect of Nocardia mitogen is exerted on the B lymphocytes. In fact, it can be shown that this product stimulates congenitally athymic "nude" mouse lymphocytes, whereas it has no activity with regard to thymus thymocytes or lymphocytes (Table IV).

TABLE IV

| Mitogen activity of Nocardia and tuberculin on mice lymphocytes. | | | | |
|---|---|---|---|---|
| Dosage of stimulant added to I.5 × 10⁶ cells | | Spleen lymphoid cells | | Thymocytes |
| | | AKR[1] | Nude | AKR |
| NWSM | 50 µg | (20) 17.98[2] ± 3.3 | (8) 17.92 ± 3.32* | (9) 1.1 ± 0.2 NS |

TABLE IV-continued
Mitogen activity of Nocardia and tuberculin on mice lymphocytes.

| Dosage of stimulant added to I.5 × 10⁶ cells | Spleen lymphoid cells AKR⁽¹⁾ | Nude | Thymocytes AKR |
|---|---|---|---|
| Tuberculin 25 μg | 1.45 ± 0.21 NS | 1.84 ± 0.47 NS | 1.1 ± 0.3 NS |

⁽¹⁾Number of mice tested individually
⁽²⁾Mean of the stimulation index ± standard deviation
*p. 0.01
NS not significant.

The results obtained with tritiated thymidine and by electron microscopy confirmed that this preparation selectively stimulates a population of B lymphocytes sensitive to cortisone.

Figure 3:
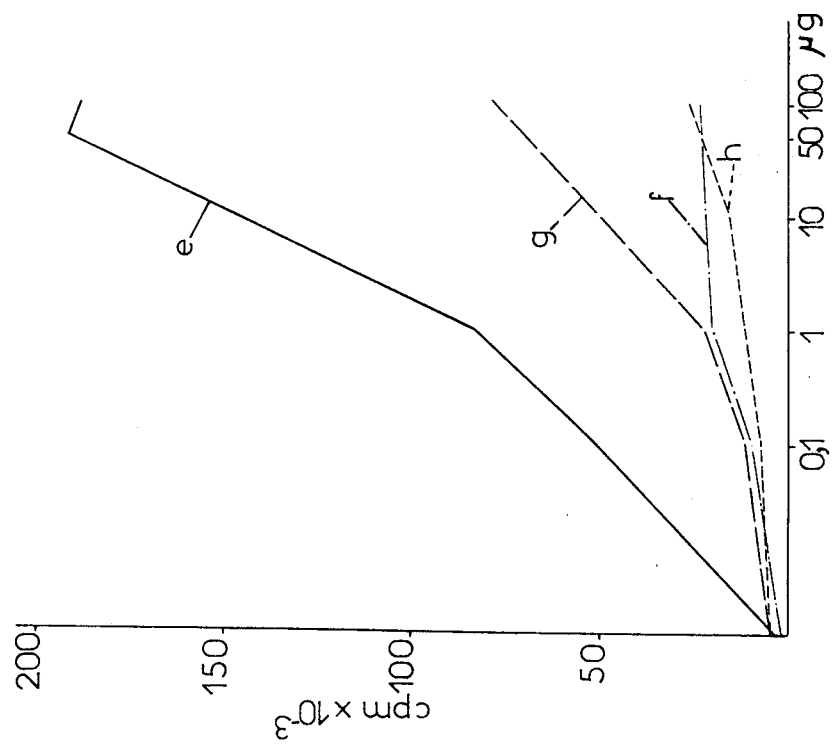
FIG. 3 shows the representative curves for spleen lymphocyte stimulation in mice produced by some of the fractions mentioned above and derived from different Nocardiae.

C. Identification of mitogenic activity of extracts derived from two other bacterial strains The following experiments showed that mouse lymphocytes can also be stimulated by extracts from *Nocardia rubra* and *Nocardia corallina* (FIG. 3). FIG. 3 gives representative curves of the variations in the mitogenic activities found by counting the radioactivity (c.p.m.) of the K peaks of N. opaca (curve e); N.corallina (curve f) and N. rubra (curve g) and the N peak of N. rubra (curve h) as a function of their respective dosages.

It can be seen from FIG. 3:
a. that of the three K peaks measured, it is the fractions from C. rubrum (or N. rubra) and especially from Nocardia opaca which are the most active. However, even though it is less active, the effect of N. Corallina is nevertheless significant;
b. that the N peak of C. rubrum is much less active than the K peak.

D. Separation of the mitogenic fraction from Nocardia opaca

Figure 4:
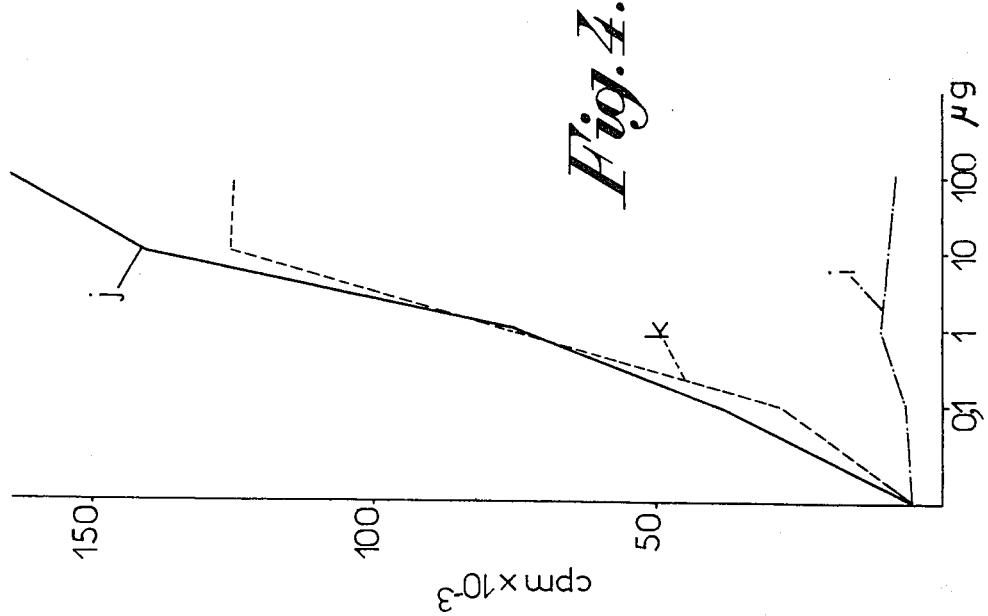
FIG. 4 shows the curves giving the mitogenic activities of the NWSM fraction (K fraction of N.opaca), and the "NWSM supernatant" (fraction P) and "NWSM deposit" (fraction Q) fractions.

The following tests show that the adjuvant activity of Nocardia can be separated from its mitogenic activity. In this study, the supernatants (curve *i* of FIG. 4) and deposit (curve *j*), obtained from the K peak (or NWSM), were analysed and compared with the same, non-centrifuged peak (curve *k*). As can be seen in FIG. 4 illustrating the variations in the radioactivity counts as a function of the dosages, the deposit is strongly active and its activity resembles that of the non-centrifuged fraction. In contrast, the supernatant, although an adjuvant, has no mitogenic activity. These effects are the same in the case of the rabbit spleen lymphocytes. Furthermore, in the case of the rabbit we found that this stimulation increases the synthesis of immunoglobulins and the differentiation of the small lymphocytes into plasmocytes.

E. Mitogenic activity of the extracts on lymphocytes from monkey or human spleen.

The mitogenic effect of 100 μg of the filtration K/peak from the Nocardia extract was also demonstrated on monkey spleen (Papio papio). In these experiments activity is also observed with the centrifugation deposit of the K peak. No increase in the incorporation of tritiated thymidine is observed in the case of the control lymphocytes incubated with tuberculin. The Nocardia extract stimulates the blastic transformation of human spleen lymphocytes.

III. Details regarding the in vitro and in vivo stimulation of marrow stem-cells NWSM was used in order to determine:
a. its ability to stimulate CFU (Colony Forming Unit) formation, that is to say the proliferation of stem-cells. For this purpose, different concentrations of NWSM were incubated with 10⁵ mouse $C_{57}B1$ bone marrow cells in the presence of mouse serum which normally contains a large amount of CSF (Colony Stimulating Factor). In this type of experiment human urine has also been used as a source of CSF.
b. Its ability to induce the formation and/or liberation of CSF in mouse blood. In this series of experiments, NWSM was injected intraperitoneally. The mouse serum was collected at different time intervals and used to stimulate the proliferation of stem-cells.

Technique:
a. Different dosages of NWSM (0.001, 0.01, 0.1, 1, 10, 100 μg) were incubated with 10⁵ bone marrow cells in the medium described by McNeill et al (Immunology, 1970, 18, 39) for 7 days.
b. the mice were injected with different dosages of NWSM and the serum was used as a source of CSF. In the case where the serum was taken at different times (30 minutes to 12 hours after the injection), the mice received 100 μg of product.

10⁵ marrow cells are incubated in 1 ml of MEM medium to which has been added 0.8% of methylcellulose, 20% of foetal calf serum, and 20% of mouse serum as a source of CSF. The colony counts were made 7 days later.

Results
1. Stimulation of the formation of colonies by NWSM. NWSM incubated with bone marrow cells in Metcalf medium without normal mouse serum does not produce the formation of colonies different from that of the control 1.5±0.9. In the presence of mouse serum as a source of CSF, the number of colonies increases considerably. The optimum concentrations of NWSM are between 1 nanogram and 1 microgram.
2. Stimulation of the formation of CSF in $C_{57}B1$ mice.
   a. Optimum dosage: NWSM was injected in different dosages into $C_{57}B1$ mice (logarithmic dilution from 1 nanogram to 100 micrograms) and blood samples were taken 6 hours later. The serum obtained was diluted to ¼.

A linear increase in the number of colonies was observed: maximum and plateau between 10 and 100 μg.
   b. Dilution of CSF: the mice are injected with 100 μg of NWSM and the serum is collected 6 hours later. The cells are incubated with serum varying in dilution from ¼ to 1/64.A maximum effect is observed up to a serum dilution of 1/16.
   c. Kinetics of the appearance of CSF after injection of NWSM: 100 μg of NWSM were injected into mice and blood samples were taken at different times.

A linear increase in the number of colonies was observed with samples of serum taken up to 6 hours after injection. With samples taken after 24 hours, a stimulation of formation of a smaller number of colonies is observed, and after 48 hours there is no effect.

d. A similar activity was observed using the deposit as the supernatant of the K peak of N. opaca and also using the K peaks of C. rubrum. The above demonstration of the various biological effects of hydrosoluble extracts of Nocardia enables the following applications to be considered:

1. as regards the non-specific mitogenic activity of the extract and more especially of the deposit of peak A:
    a. a very valuable hydrosoluble and non-toxic biological research agent, enabling the stimulation of B lymphocytes in various animal species, including monkeys and man, to be effected.

It will be remembered that lipopolysaccharides (endotoxins of Gram negative bacteria) are toxic and, even though they stimulate rabbit lymphocytes, they have no effect in the case of rabbits, monkeys and man.

b. a medical biological agent.; The use of this product can be envisaged for diagnosing, using lymph organ cells, immunity deficiency with regard to antibody-producing cells.

c. preventative treatment: after animals have been injected with the product, an overall non-specific stimulation is observed producing an increase in the number of antibodies against a large range of antigens.

2. As regards the ability to stimulate the formation of stem-cells its use can be envisaged in the curative treatment of bone marrow deficiency diseases resulting from accidental (e.g. irradiation or idiopathic (e.g. myelosclerosis) causes.

The fact that it is possible to use the mitogenic hydrosoluble product without adding oily carriers, and the absence of toxicity, make it a particularly useful therapeutic agent.

It is preferably administered by injection in combination with sterile injectable liquid carriers such as isotonic saline solution or isotonic glucose solution.

It is of course obvious, and furthermore follows from what has already been said, that the invention is not limited solely to those methods of application and embodiments which have more especially been considered; on the contrary, it covers all possible variations.

We claim:

1. In the process for preparing a water-soluble agent which comprises treating an aqueous suspension of delipidated Nocardia cells with a muramidase to free the mitogenic agent and immunological non-specific adjuvant peptidoglycane and other adjuvant fragments that were contained therein, separating the solid fraction from the mixture, recovering the aqueous mixture containing the mitogenic agent and immunological non-specific adjuvant peptidoglycane fragments, the improvement comprising:

separating from the aqueous mixture the portion containing the adjuvant peptidoglycane fragments, which adjuvant is soluble in concentrated acetic acid, and recovering the remaining fraction which contains the mitogenic agent, said agent being insoluble in concentrated acetic acid.

2. The process of claim 1 which comprises the additional step of lyophilizing the aqueous portion before separating the adjuvant peptidoglycane fragments therefrom.

3. The process of claim 2 which comprises the additional step of delipidating the cells before lyophilizing.

4. The process of claim 1 which comprises the additional step of purifying by filtration with a molecular sieve the aqueous portion before separating the adjuvant peptidoglycane fragments therefrom.

5. The process of claim 4 wherein said fractionating comprises filtering through a molecular sieve column.

6. The process of claim 1 wherein separating the adjuvant peptidoglycane fragments from the aqueous portion is performed by suspending the aqueous portion in concentrated acetic acid.

7. The process of claim 1 which comprises the further step of separating the supernatant from the deposit prior to collecting the deposit.

8. The process of claim 6 which comprises the further step of recovering by redissolving in water the acetic acid-insoluble fraction which contains the mitogenic agent, and which is water soluble.

9. The process of claim 8 wherein the recovery step is carried out by gravity.

10. A mitogenic agent from delipidated Nocardia cells which is free of peptidoglycane fragments which have adjuvant activity, are soluble in concentrated acetic acid and which agent is active in vivo, water-soluble concentrated acetic acid-insoluble and which is capable of stimulating B-lymphocytes and the proliferation of stem cells.

11. The aqueous solution of the agent of claim 10.

12. The agent of claim 10 which is non-toxic.

13. A pharmaceutical composition which is a non-toxic, injectable preparation of the agent of claim 10 in combination with a pharmaceutically acceptable carrier.

14. An immunological process for stimulating lyphocytes which comprises contacting them with the mitogenic composition of claim 10.

15. An immunological process for stimulating lymphocytes in vivo by administering the agent of claim 10 to warm-blooded animals.

16. An immunological process for stimulating the formation of stem cells which comprises contacting them with the agent of claim 10.

17. An immunological process for stimulating the proliferation of stem cells which comprises contacting them with the agent of claim 10.

18. An immunological process for treating bone marow deficiency diseases due to a deficiency in stem cells which comprises administering an injectable solution of the agent of claim 10 to a warm-blooded mammal.

19. An immunological process for diagnosing immunodeficiencies with regard to antibody-producing cells which comprises contacting lymph organ cells with the agent of claim 10.

20. An immunological process for treating bone marrow deficiency diseases due to deficiency in stem cells which comprises administering a dose of the agent of claim 10 effective to stimulate lymphocytes and to stimulate the prolification of stem cells.

21. The pharmaceutical composition of claim 13 wherein the carrier is an aqueous solution.

22. The pharmaceutical composition of claim 21 wherein the composition is free of oily carrier.

* * * * *